United States Patent
Sermone et al.

(10) Patent No.: US 11,571,396 B2
(45) Date of Patent: Feb. 7, 2023

(54) KETAMINE FOR TREATMENT OF ADNP SYNDROME AND SENSORY PROCESSING DEFICITS

(71) Applicants: Sandra Sermone, Brush Prairie, WA (US); Matthew Davis, Brush Prairie, WA (US)

(72) Inventors: Sandra Sermone, Brush Prairie, WA (US); Matthew Davis, Brush Prairie, WA (US)

( * ) Notice: Subject to any disclaimer, the term of this patent is extended or adjusted under 35 U.S.C. 154(b) by 0 days.

(21) Appl. No.: 16/827,521

(22) Filed: Mar. 23, 2020

(65) Prior Publication Data

US 2020/0297662 A1    Sep. 24, 2020

Related U.S. Application Data

(60) Provisional application No. 62/822,822, filed on Mar. 23, 2019, provisional application No. 62/857,210, filed on Jun. 4, 2019.

(51) Int. Cl.
*A61K 31/135* (2006.01)
*A61P 25/00* (2006.01)

(52) U.S. Cl.
CPC .......... *A61K 31/135* (2013.01); *A61P 25/00* (2018.01)

(58) Field of Classification Search
CPC .............................. A61K 31/135; A61P 25/00
See application file for complete search history.

(56) References Cited

U.S. PATENT DOCUMENTS

| | | | | |
|---|---|---|---|---|
| 4,994,467 A * | 2/1991 | Zimmerman | ........ | A61K 31/135 514/284 |
| 7,452,867 B2 | 11/2008 | Gozes et al. | | |
| 7,960,334 B2 | 6/2011 | Gozes et al. | | |
| 8,143,221 B2 | 3/2012 | Gozes et al. | | |
| 8,377,875 B2 | 2/2013 | Gozes et al. | | |
| 8,586,548 B2 | 11/2013 | Gozes | | |
| 8,618,043 B2 | 12/2013 | Gozes et al. | | |
| 9,518,994 B2 | 12/2016 | Gozes et al. | | |
| 10,118,943 B2 | 11/2018 | Gozes et al. | | |
| 2007/0054847 A1* | 3/2007 | Gozes | ............. | A61K 38/18 514/8.4 |
| 2012/0010148 A1 | 1/2012 | Gozes et al. | | |
| 2015/0196501 A1 | 7/2015 | Erickson et al. | | |
| 2017/0095429 A1 | 4/2017 | Erickson et al. | | |
| 2018/0344809 A1 | 12/2018 | Gozes | | |

FOREIGN PATENT DOCUMENTS

| | | | | |
|---|---|---|---|---|
| EP | 2521919 A2 | 11/2012 | | |
| WO | WO-2014117089 A1 * | 7/2014 | ............. | A61K 31/13 |
| WO | WO-19/006161 A1 | 1/2019 | | |
| WO | WO-20/198039 A1 | 10/2020 | | |
| WO | WO-20/247615 A1 | 12/2020 | | |

OTHER PUBLICATIONS

Genesis Behavior Center, "How Autism and Sensory Processing Disorder Are Linked", publ online Aug. 2016, pp. 1-6, http: https://genesisbehaviorcenter.com/how-autism-and-sensory-processing-disorder-are-linked/ (Year: 2016).*

Mandel, S., et al., "Activity-dependent neuroprotective protein (ADNP) differentially interacts with chromatin to regulate genes essential for embryogenesis," Developmental Biology, vol. 303, pp. 814-824 (2007).

Helsmoortel, C., et al., "A SWI/SNF related autism syndrome caused by de novo mutations in ADNP," Nat. Genet., vol. 46, No. 4, pop. 380-384, (Apr. 2014)—Author Manuscript available in PMC Oct. 1, 2014 (15 total pages).

Arnett, A.B., et al., "The Autism Spectrum Phenotype in ADNP Syndrome," Austism Res., vol. 11, No. 9, pp. 1300-1310 (Sep. 2018)—Author Manuscript available in PMC Sep. 1, 2019 (12 total pages).

Zamostiano, R., et al., "Cloning and Characterization of the Human Activity-dependent Neuroprotective Protein*," The Journal of Biological Chemistry, vol. 276, pp. 708-714, first published on Sep. 29, 2000, downloaded from https://www.jbc.org/content/276/1/708.long (9 total pages).

Gennet, N., et al., "Expression of activity-dependent neuroprotective protein in the brain of adult rats," Histology and Histopathology—Cellular and Molecular Biology, vol. 23, pp. 309-317 (2008).

Oz, S., et al., "The NAP motif of activity-dependent neuroprotective protein (ADNP) regulates dendritic spines through microtubule end binding proteins," Molecular Psychiatry, vol. 19, pp. 1115-1124 (2014).

Fava, M., et al., "Double-Blind, Placebo-Controlled, Dose-Ranging Trial of Intravenous Ketamine as Adjunctive Therapy in Treatment-Resistant Depression (TRD)," Mol. Psychiatry, Author Manuscript available in PMC Apr. 4, 2019 (20 total pages).

Spravato®, Highlights of Prescribing Information, Janssen Pharmaceutical Companies, New Jersey, U.S.A., 41 total pages issued by U.S. Food and Drug Administration (Mar. 2019).

Kurdi, M.S., et al., "Ketamine: Current applications in anesthesia, pain, and critical care," Anesth. Essays Res., vol. 8, No. 3, pp. 283-290 (Sep.-Dec. 2014)—downloaded from https://www.ncbi.nlm.nih.gov/pmc/articles/PMC4258981/, last retrieved on May 27, 2020, pp. 1-11.

Turner, C.P., et al., "Strategies to defeat ketamine-induced neonatal brain injury," Neuroscience, vol. 210, pp. 384-392 (May 17, 2012)—Author Manuscript available in PMC May 17, 2013 (18 total pages).

Brown, B.P., et al., "In Vivo and In Vitro Ketamine Exposure Exhibits a Dose-Dependent Induction of Activity-Dependent Neuroprotective Protein in Rat Neurons," Neuroscience, vol. 290, pp. 31-40 (available online Jan. 13, 2015).

Blaj, C., et al., "ADNP Is a Therapeutically Inducible Repressor of WNT Signaling in Colorectal Cancer," Clin. Cancer Res., vol. 23, No. 11, pp. 2769-2780 (first published online Nov. 30, 2016).

Vulih-Shultzman, I. et al., "Activity-Dependent Neuroprotective Protein Snippet NAP Reduces Tau Hyperphosphorylation and Enhances Learning in a Novel Transgenic Mouse Model," J. Pharmacol. Exp. Ther., vol. 323, No. 2, pp. 438-449, doi: 10.1124/jpet.107.129551 (accepted Aug. 23, 2007).

(Continued)

*Primary Examiner* — Sarah Pihonak

(57) ABSTRACT

A method of treating sensory processing disorder, autism spectrum disorder, and/or ADNP syndrome comprising the administration of low doses of ketamine and/or low doses of ketamine and NAP.

6 Claims, No Drawings

(56) References Cited

OTHER PUBLICATIONS

Amram, N., et al., "Sexual Divergence in Microtubule Function: The Novel Intranasal Microtubule Targeting SKIP Normalizes Axonal Transport and Enhances Memory," Mol. Psychiatry, vol. 21, pp. 1467-1476, doi: 10.1038/mp.2015.208 (published online Jan. 19, 2016).

Ivashko-Pachima, Y., et al., "ADNP/NAP Dramatically Increase Microtubule End-Binding protein-Tau Interaction: A Novel Avenue for Protection Against Tauopathy," Mol. Psychiatry, vol. 22, pp. 1335-1344, doi: 10.1038/mp.2016.255 (published online Jan. 24, 2017).

Chen, M.H., et al., "Antisuicidal Effect, BDNF Val66Met Polymorphism, and Low-Dose Ketamine Infusion: Reanalysis of Adjunctive Ketamine Study of Taiwanese Patients With Treatment-Resistant Depression (AKSTP-TRD)," J. Affect. Disord., vol. 251, pp. 162-169, doi: 10.1016/j.jad.2019.03.075, (available online Mar. 23, 2019).

Yan, J. and Jiang, H., "Dual Effects of Ketamine: Neurotoxicity Versus Neuroprotection in Anesthesia for the Developing Brain," Journal of Neurosurgical Anesthesiology, vol. 26, No. 2, pp. 155-160 (Apr. 2014).

Sragovich, S., et al., "The autism-mutated ADNP plays a key role in stress response," Translational Psychiatry, vol. 9, No. 235, pp. 1-12 (2019).

Kapitansky, O., "Single Cell ADNP Predictive of Human Muscle Disorders: Mouse Knockdown Results in Muscle Wasting," Cells, vol. 9, No. 2320, pp. 1-25 (Oct. 19, 2020).

Grigg, I., et al., "Tauopathy in the young autistic brain: novel biomarker and therapeutic target," Transl. Psychiatry, vol. 10, No. 228, 10 total pages (2020).

Ivashko-Pachima, Y., et al., "Deciphering the Enigma: NAP (CP201) the Active ADNP Drug Candidate Enters Cells by Dynamin-Associated Endocytosis,," J. Mol. Neurosci., vol. 70, pp. 993-998 (published online Jun. 26, 2020).

Heimesaat, M.M., et al., "Immune-modulatory Properties of the Octapeptide NAP in Campylobacter jejuni Infected Mice Suffering from Acute Enterocolitis," Microorganisms, vol. 8, No. 802, pp. 1-18 (May 26, 2020).

Kapitansky, O., et al., "Microbiota changes associated with ADNP deficiencies: rapid indicators for NAP (CP201) treatment of the ADNP syndrome and beyond," J. Neural. Transm., vol. 127, pp. 251-263 (published online Feb. 18, 2020).

Ivashko-Pachima, et al., "Discovery of autism/intellectual disability somatic mutations in Alzheimer's brains: mutated ADNP cytoskeletal impairments and repair as a case study," Molecular Psychiatry, 15 total pages (published online Oct. 30, 2019).

Levine, J., et al., "Developmental Phenotype of the Rare Case of DJ Caused by a Unique ADNP Gene De Novo Mutation," Journal of Molecular Neuroscience, vol. 68, pp. 321-330 (published online May 24, 2019).

Yang, M.H., et al., "Reduction of aluminum ion neurotoxicity through a small peptide application—NAP treatment of Alzheimer's disease," Food Drug Anal., vol. 27, pp. 551-564 (available online Jan. 12, 2019).

Ivashko-Pachima, Y., et al., "NAP (davunetide) preferential interaction with dynamic 3-repeat Tau explains differential protection in selected tauopathies," PLoS ONE, vol. 14, No. 3, e0213666, pp. 1-20 (Mar. 13, 2019).

Mollinedo, P., et al., "Cellular and animal models of skin alterations in the autism-related ADNP syndrome," Scientific Reports, vol. 9, No. 736, pp. 1-10 (published online Jan. 24, 2019).

Sragovich, et al., "The autism/neuroprotection-linked ADNP/NAP regulate the excitatory glutamatergic synapse," Translational Psychiatry, vol. 9, No. 2, pp. 1-14 (2019).

Gozes, I., "ADNP Regulates Cognition: A Multitasking Protein," Frontiers in Neuroscience, vol. 12, Article 873, pp. 1-5 (Nov. 2018).

Ivashko-Pachima, Y., et al., "NAP Protects against Tau Hyperphosphorylation Through GSK3," Curr. Pharm., vol. 24, pp. 3868-3877 (accepted Nov. 5, 2018) (10 total pages).

Hacohen-Kleiman, G., et al., "Activity-dependent neuroprotective protein deficiency models synaptic and developmental phenotypes of autism-like syndrome," J. Clin. Invest., vol. 128, No. 11, pp. 4956-4969 (Nov. 2018).

Ziv, Y., "Activity-dependent neuroprotective protein (ADNP) is an alcohol-responsive gene and negative regulator of alcohol consumption in female mice," Neuropsychopharmacology, vol. 44, pp. 415-424 (published online Jun. 27, 2018).

Alm, A., and Villumsen, J., "Effects of Topically Applied PGF2alpha and its Isopropylester on Normal and Glaucomatous Human Eyes," The Ocular Effects of Prostaglandins, pp. 447-458 (1989).

Coe, B.P., et al., "Refining analyses of copy number variation identifies specific genes associated with developmental delay," Nature Genetics, vol. 46, No. 10, pp. 1063-1071—11 total pages with "Online Methods" (Oct. 2014).

Fitzgerald, T. W et al., "Large-scale discovery of novel genetic causes of developmental disorders," Nature, vol. 519, No. 7542, pp. 223-228 (Mar. 12, 2015)—Author Manuscript availble in PMC May 16, 2018 (27 total pages).

International Search Report and Written Opinion prepared by U.S. Patent and Trademark Office as International Searching Authority for International Patent App. No. PCT/US2020/023947, dated Jun. 16, 2020 (8 total pages).

International Search Report and Written Opinion prepared by U.S. Patent and Trademark Office as International Searching Authority for International Patent App. No. PCT/US2020/036103, dated Oct. 9, 2020 (12 total pages).

Mordenti, J., et al., "Intraocular Pharmcokinetics and Safety of a Humanized Monoclonal Antibody in Rabbits after Intravitreal Administration of a Solution or a PLGA Microsphere Formulation," Toxicol. Sci., vol. 52, pp. 101-106 (1999).

Ostapcuk, V., et al. , "Activity-dependent Neuroprotective Protein Recruits HP1 and CHD4 to Control Lineage-specifying Genes," Nature, vol. 557, pp. 739-743 with Methods and Reporting Summary (26 total pages), doi.org/10.1038/S41586-018-0153-8 (May 31, 2018).

Quraishe, S., et al., "Microtubule stabilising peptides rescue tau phenotypes in-vivo," Scientific Reports, vol. 6, No. 38224, pp. 1-9 (Dec. 2, 2016) with Corrigenndum (updated Feb. 1, 2017).

\* cited by examiner

KETAMINE FOR TREATMENT OF ADNP SYNDROME AND SENSORY PROCESSING DEFICITS

Embodiments herein relate to the field of treatment of autism and, more specifically, to the treatment of sensory processing disorders and ADNP Syndrome.

The present invention relates to novel compositions and methods for delivering them to individuals with autism who exhibit disordered processing of sensory input, commonly referred to as sensory processing disorder, and/or ADNP Syndrome. Sensory processing disorder can manifest as oversensitivity to sensory input, such as sound or touch, or an excessive or compulsive seeking of sensory input. The present invention relates to novel compositions and methods for delivering either (1) ketamine as a single pharmaceutical treatment, or (2) ketamine/NAP (a neuroprotective peptide derived from activity-dependent neuroprotective protein) as a combination pharmaceutical treatment for individuals with ADNP Syndrome, which include mutations and deletions and refer to any change in the ADNP gene, as well as FOXP1 and/or FOXP@ and other associated conditions which exhibit a combination of similar neurological abnormalities, neurological degeneration, neurological dysfunction, neurodevelopmental dysfunction, motor dysfunction, speech dysfunction, and autism.

The activity-dependent neuroprotector gene (ADNP gene) encodes a protein called the activity-dependent neuroprotector homeobox. Human mutation in ADNP, including mutation in exon 5 of ADNP, is correlated with developmental, motor, intellectual and speech delays as well as autism spectrum disorder and other related behavioral conditions. Individuals exhibiting autism and/or sensory processing disorder associated with a mutation in ADNP have a dysfunctioning gene which is thought to disrupt the levels of the ADNP protein, resulting in at least some cases with low levels of ADNP protein in the brain. ADNP is currently the most prevalent single gene cause of autism spectrum disorder. The majority of individuals with autism associated with ADNP mutations have mild to severe sensory processing disorders. ADNP disorder is also known to be related to other neurological conditions such as Alzheimer's and schizophrenia.

It has been observed that anesthetic doses of ketamine induce gene expression of ADNP. Ketamine is a dissociative anesthetic. It is a non-competitive N-methyl-d-aspartate (NMDA) antagonist that disrupts calcium homeostasis in neurons. It can be a neurotoxin in some animal models as well as a neuroprotectant in other animal models, and depending on the dosage, it has been demonstrated to be protective as well as destructive to certain brain regions. ADNP gene expression has been observed to increase 1.5 fold in the somatosensory cortex of post-natal day 7 rats following a sedative dose of ketamine or MK801. Increase in gene expression has been associated with higher levels of ADNP protein.

The somatosensory cortex has a significant role in the sensory system in the human body, including a role in sensory processing. Individuals with an ADNP mutation who exhibit abnormal sensory behaviors due to autism and/or sensory processing disorder, may have reduced levels of ADNP protein in the somatosensory cortices. An increase in ADNP protein levels in the somatosensory cortex could cause or be associated with amelioration of sensory processing disorders and/or the symptoms associated with sensory processing disorders such as sensation-seeking or sensation-avoiding behaviors.

Ketamine administration results in the dysregulation of calcium homeostasis, providing a neuronal stressor. In cells without ADNP mutations, the neurons respond by further upregulating ADNP, which would be very promising for patients with ADNP syndrome and other related conditions who may have a reduction in the ADNP. An increase in ADNP expression and protein levels could cause or be associated with amelioration of symptoms associated with changes or deletions of the ADNP gene, and other related conditions as described in section 0001.

Administration of low doses of ketamine have been observed to induce ADNP expression, and have been observed to increase ADNP protein levels, including in the somatosensory cortex. The inventors believe that administration of sub-anesthetic doses of ketamine, alone or together with other therapeutic agents, will increase ADNP protein levels in the somatosensory cortex and improve sensory processing and/or ameliorate the symptoms of sensory processing disorder in individuals with autism and or sensory processing disorders associated with ADNP mutations. Accordingly, the inventor has invented and discloses herein a method of treating sensory processing disorder in individuals with autism and/or sensory processing disorder associated with ADNP mutation by administering a sub-anesthetic dose of ketamine.

The ADNP derived peptide NAP (NAPVSIPQ) has been shown to enhance the invasion of dynamic microtubules into growth cones. We suspect that the growth cones do not collapse in the presence of low concentrations of ketamine because of the potential microtubule stabilization-promoting ability of the NAP domain of ADNP. Neurons treated with a low concentration of ketamine demonstrated both stably expanded growth cones and a significant increase in ADNP in neurites. Nuclear ADNP was more abundant than cytoplasmic ADNP, and the primary increase in ADNP occurred in the nucleus following ketamine treatment. We believe that low-dose ketamine, by inducing ADNP, does more than could be with NAP alone.

A low concentration ketamine exposure (50 or 100 µM) notably increased the total cellular ADNP levels. At 50 µM, negative effects of decreased growth cones were not observed, yet ADNP levels were increased at a rate equivalent to higher ketamine dosing.

Ketamine to treat sensory processing disorder and/or autism and related disorders may be administered in a does as low as 0.1 mg/kg and up to 1.0 mg/kg. Dose administration sessions may range between 2 and 100 minutes in duration. The drug may be administered intramuscularly, subcutaneously, or intravenously. More preferably, oral, sublingual, transmucosal, or intranasal routes may be employed.

ADNP induction may be partially responsible for the efficacy of a low-dose ketamine pre-treatment in preventing ketamine-induced neuronal cell death. High-dose ketamine levels induce apoptosis, as well as expression of ADNP in rats. Low-dose ketamine increases ADNP levels and prevents caspase-3 activation in the hippocampus and somatosensory cortex. Low dose ketamine (5 mg/kg) blocks high dose ketamine induced injury, as does NAP administration. It is therefore theorized that low-dose ketamine prevents high-dose ketamine injury at least in part by increasing expression of ADNP.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A method of treating sensory processing disorder associated with an under-expression or reduction of the ADNP protein, the method comprising administering ketamine in a sub-anesthetic dose to an individual having sensory processing disorder with disrupted ADNP protein levels.

2. The method of claim 1 wherein the ketamine is administered in a dose of 0.1 mg/kg to 1.0 mg/kg.

3. The method of claim 1 further comprising administering NAP to the individual.

4. The method of claim 2 wherein the ketamine is administered in a session that ranges between 2 and 100 minutes in duration.

5. The method of claim 1 wherein the ketamine is administered via a route selected from the group consisting of oral, sublingual, transmucosal, intranasal, intramuscular, subcutaneous, intravenous, and combinations thereof.

6. The method of claim 5, wherein the ketamine is administered via a route selected from the group consisting of oral, sublingual, transmucosal, intranasal, and combinations thereof.

* * * * *